(12) United States Patent
Augarten (10) Patent No.: US 12,396,618 B2
(45) Date of Patent: Aug. 26, 2025

(54) DYNAMIC LIGHT SOURCE STATUS INDICATION FOR ENDOSCOPIC SYSTEMS

(71) Applicant: KARL STORZ Imaging, Inc., Goleta, CA (US)

(72) Inventor: Michael Augarten, Goleta, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 259 days.

(21) Appl. No.: 17/454,219

(22) Filed: Nov. 9, 2021

(65) Prior Publication Data

US 2023/0146673 A1 May 11, 2023

(51) Int. Cl.
*A61B 1/00* (2006.01)
*A61B 1/06* (2006.01)
*A61B 1/07* (2006.01)
*G16H 40/63* (2018.01)

(52) U.S. Cl.
CPC ...... *A61B 1/00006* (2013.01); *A61B 1/00039* (2013.01); *A61B 1/0669* (2013.01); *A61B 1/0684* (2013.01); *A61B 1/07* (2013.01); *G16H 40/63* (2018.01)

(58) Field of Classification Search
CPC ............ A61B 1/00006; A61B 1/00039; A61B 1/00059; A61B 1/00117; A61B 1/00121; A61B 1/00126; A61B 1/07; A61B 1/00025; A61B 1/00036; A61B 1/06; A61B 1/0661; A61B 1/0655; A61B 1/0669; A61B 1/0676; A61B 1/0684; G16H 40/63
See application file for complete search history.

(56) References Cited

U.S. PATENT DOCUMENTS

| | | | |
|---|---|---|---|
| 5,850,496 A * | 12/1998 | Bellahsene | A61B 1/00126 385/101 |
| 6,110,107 A * | 8/2000 | Bellahsene | A61B 1/0669 385/101 |
| 6,511,422 B1 * | 1/2003 | Chatenever | A61B 1/0661 600/180 |
| 6,658,577 B2 | 12/2003 | Huppi | |
| 8,372,003 B2 | 2/2013 | St. George | |
| 8,537,210 B2 | 9/2013 | Omori | |
| 8,878,920 B2 | 11/2014 | Ovod | |
| 9,459,415 B2 | 10/2016 | Feingold | |
| 9,770,163 B2 | 9/2017 | Ovod | |
| 2002/0178388 A1 * | 11/2002 | Huppi | G06F 1/1684 713/300 |
| 2004/0210112 A1 * | 10/2004 | Ota | A61B 1/0684 600/178 |

(Continued)

*Primary Examiner* — Ryan N Henderson
(74) *Attorney, Agent, or Firm* — David N. Villalpando; Jacqueline Cohen (57) ABSTRACT

A light source for an endoscope system includes a receptacle for receiving a first end of a light guide cable, a light engine with at least one LED configured to provide light transmitted from the first end of the light guide cable to a second end of the light guide cable connected to an endoscope, and a light output controller configured to adjust an intensity level of the light engine according to a set intensity level when an imaging mode is selected and at least one auxiliary mode to indicate to the user a status of the system such as a standby mode, a disconnected light guide cable, or additional statuses related to the functioning of the endoscope system.

16 Claims, 6 Drawing Sheets

(56) References Cited

U.S. PATENT DOCUMENTS

| | | | |
|---|---|---|---|
| 2007/0088193 A1* | 4/2007 | Omori | A61B 1/00126 |
| | | | 600/101 |
| 2007/0149857 A1* | 6/2007 | Yabe | A61B 1/00059 |
| | | | 600/117 |
| 2010/0228089 A1* | 9/2010 | Hoffman | H01S 5/06808 |
| | | | 372/38.07 |
| 2011/0208004 A1* | 8/2011 | Feingold | A61B 1/00045 |
| | | | 600/178 |
| 2013/0016200 A1* | 1/2013 | Ovod | H04N 23/74 |
| | | | 348/E7.085 |
| 2014/0012078 A1 | 1/2014 | Coussa | |
| 2014/0200406 A1* | 7/2014 | Bennett | A61B 1/0646 |
| | | | 600/109 |
| 2014/0296628 A1* | 10/2014 | Kirma | A61B 1/0655 |
| | | | 600/103 |
| 2014/0328063 A1* | 11/2014 | Nishio | G02B 6/0005 |
| | | | 362/555 |
| 2017/0188802 A1* | 7/2017 | Lawrence | A61B 1/0607 |
| 2018/0199805 A1* | 7/2018 | Sakanoue | H04N 23/667 |
| 2018/0263470 A1* | 9/2018 | Miyazaki | H04N 23/56 |
| 2021/0278659 A1* | 9/2021 | Deng | G02B 23/2476 |
| 2022/0175232 A1* | 6/2022 | Müller | A61B 90/361 |
| 2023/0284890 A1* | 9/2023 | Niwa | A61B 1/0655 |
| 2024/0122449 A1* | 4/2024 | Sharma | A61B 1/045 |
| 2024/0345339 A1* | 10/2024 | Feingold | A61B 1/00009 |

* cited by examiner

DYNAMIC LIGHT SOURCE STATUS INDICATION FOR ENDOSCOPIC SYSTEMS

FIELD

This disclosure relates to light sources for endoscopic imaging systems and in particular, using an endoscopic light source to indicate a status of the endoscopic imaging system.

BACKGROUND

The imaging of body surfaces through an endoscope is well known within the medical and veterinarian fields. Typically, this involves inserting an endoscope into a body cavity and directing a high intensity light source output through the endoscope to illuminate body tissue. Light reflected by the body tissue is then guided along an optical path to an image sensor to generate both video and still images of the tissue. One such approach, described in U.S. Pat. No. 5,162,913 to Chatenever et al., provides a technique for an automatic adjustment of the exposure of video images detected with an image sensor.

The use of high intensity light sources involves potential hazards to medical personnel and patients. Light sources in the past have included light driver systems which may use metal-halide, halogen, xenon, or other high energy bulbs that generate significant heat both in the light source and along the light guide cable. Many light sources now use LED light driver systems which still generate significant heat. In some instances, a light guide cable is used to convey the high intensity-light source output to an endoscope. The cable may be momentarily disconnected from the endoscope and placed on a sterile drape used to protect the patient. The high intensity light output can be sufficient to ignite the drape and pose a fire hazard. In other instances, the user can inadvertently hold the disconnected light guide cable in such a way as to temporarily blind another person in the room or burn tissue of a patient or the user. In some instances, when the endoscope is removed from (i.e., pulled out of) a patient, there can be a risk of these same hazards.

When the light source is used with an endoscopic video camera, which has an automatic exposure system, the light source output intensity may be turned up to an intensity level higher than required for the camera to produce well-exposed images. If the light guide cable becomes disconnected, the automatic exposure system may detect a decrease in brightness and cause the light source to increase intensity further to compensate. This increased light intensity level can burn body tissue and cause serious injury to the patient.

In some instances, a light source may enter a standby mode to prevent the above-mentioned potential hazards from materializing. The standby mode may be triggered in response to a detection of a disconnected light guide cable. Alternatively, the standby mode may be selected by the user at the conclusion of a procedure or default to standby mode when powered on. In standby mode, the light source may be set to a reduced output level of lower intensity light output. Depending on ambient lighting conditions, the reduced output level may make it difficult for a user or bystander to determine if the light source is in standby mode, is in operational mode but at a low level of output, or in some circumstances, is turned off. In situations with a high level of ambient lighting, this could be exacerbated.

In other situations, the light source may provide non-visible illumination. For example, in some imaging modes, the light source may output excitation light in the infrared or ultraviolet light range. This excitation light may be used to excite a dye present in the body or a specific tissue such as a cancerous mass. In these situations, the user may be unaware that the light source is generating this non-visible light energy and that the light guide could be hot. In still other situations, the light source may provide a spectral range of illumination transgressing a broad spectrum of bandwidths, both visible and non-visible. For example, in hyperspectral and multispectral imaging, a variety of hues and colors of light may be emitted by the light source at varying intensities in order to elicit varying responses from the tissue and detected reflectance by the image sensor.

Techniques have been proposed to reduce the risks associated with high intensity light sources with disconnected light guide cables. One approach to solve this problem is described in U.S. Pat. No. 5,850,496 to Bellahsene et al. (hereinafter Bellahsene '496). Bellahsene '496, herein incorporated by reference, describes a light guide cable with two conductors running along its length but not in direct electrical contact with each other. Contacts at one end of the cable attach to circuitry internal to the light source while contacts at the other end of the cable attach to the endoscope. When the light guide cable is connected to the light source and the endoscope, the two conductors are shorted together to complete the circuit. When the light guide cable becomes disconnected from the endoscope, the circuit is broken. The light source may detect the broken circuit and determine the light guide cable is connected. The light source may then be forced into a standby mode in which the intensity of light output is reduced.

One approach to solve this problem is described in U.S. Pat. No. 6,511,422 to Chatenever (hereinafter Chatenever '422). Chatenever '422, herein incorporated by reference, describes a method and apparatus where the output from a high intensity light source is controlled so that whenever the output is not directed at tissue (meaning that the endoscope/video camera/light source combination is not currently being used to image body tissue), the light source output intensity is automatically reduced to a safer level. This is done by monitoring the reflected light from tissue and when this reflection indicates that the light source is not directed at tissue, the light intensity is turned down to a safer level. This involves generating a modulation signal and modulating the intensity of the light source output with the modulation signal.

However, none of these solutions provides any clear indication to the user of the status of the light source. For example, should the light guide cable become disconnected, the light source may remain on and at whatever intensity level was previously set. Alternately, in some circumstances such as those disclosed by Chatenever '422, the light source may be reduced to a "safe" level yet still outputting some amount of light when in standby mode. Although the light source may include a display which may relay to the user that status of the light source, the display may be at some distance from the user or otherwise blocked from view. Thus, the user may not be able to discern the actual status of the light source and depending on lighting in the operating room, may not be able to distinguish a light source that is on, off, in a standby mode, or accidentally disconnected from the endoscope and still on.

SUMMARY

Accordingly, the endoscopic imaging system of the present disclosure includes features which provide a clear indication to the user of the status of the light source and the light guide cable using the light source illumination.

In one example, a light source for an endoscope system includes a receptacle for receiving a first end of a light guide cable, a light engine with at least one LED configured to provide light transmitted from the first end of the light guide cable to a second end of the light guide cable connected to an endoscope, and a light output controller configured to adjust an intensity level of the light engine according to a set intensity level when an imaging mode is selected and a first auxiliary mode when a standby mode is selected.

In other features, the first auxiliary mode adjusts the intensity level according to a time-based function routine. The time-based function routine includes a repeating, non-linear duty cycle in which the light output controller adjusts the intensity level to increase and decrease in a manner that mimics breathing. In still other features, the time-based function routine includes a repetition of a series of duty cycle pulses, each pulse having a maximum duty cycle and a minimum duty cycle and including pulse widths varying in accordance with a non-linear duty cycle function, the non-linear duty cycle function including a positively biased sinusoidal function.

In yet other features, the light source includes a light source input configured to accept user input to select the standby mode and adjust the set intensity level.

In yet other features, the light source includes a connection monitor configured to determine when the second end of the light guide cable is connected to the endoscope or disconnected from the endoscope. In still other features, when the connection monitor detects a disconnected light guide cable, the light output controller selects a second auxiliary mode that adjusts the intensity level according to a blinking routine. The blinking routine includes a repeating duty cycle ranging from a minimum duty cycle to a maximum duty cycle, the minimum duty cycle active for a blink off time and the maximum duty cycle active for a blink on time.

In another example, a light source for an endoscope system includes a receptacle for receiving a first end of a light guide cable, a light engine with at least one LED configured to provide light transmitted from the first end of the light guide cable to a second end of the light guide cable connected to an endoscope, and a light output controller configured to adjust an intensity level of the light engine according to a set intensity level when an imaging mode is selected and a first auxiliary mode when the second end of the light guide cable is disconnected.

In other features, the light source includes a connection monitor configured to determine when the second end of the light guide cable is connected to the endoscope or disconnected from the endoscope. The first auxiliary mode adjusts the intensity level according to a blinking routine. The blinking routine includes a repeating duty cycle ranging from a minimum duty cycle to a maximum duty cycle, the minimum duty cycle active for a blink off time and the maximum duty cycle active for a blink on time.

In yet other features, the light output controller is further configured to adjust the intensity level according to a second auxiliary mode when a standby mode is selected. The second auxiliary mode adjusts the intensity level according to a time-based function routine. The time-based function routine includes a repeating, non-linear duty cycle in which the light output controller adjusts the intensity level to increase and decrease in a manner that mimics breathing. In still other features, the time-based function routine includes a repetition of a series of duty cycle pulses, each pulse having a maximum duty cycle and a minimum duty cycle and including pulse widths varying in accordance with a non-linear duty cycle function, the non-linear duty cycle function including a positively biased sinusoidal function.

In yet other features, the light source includes a light source input configured to accept user input to select the standby mode and adjust the set intensity level.

In another example, a light source for an endoscope system includes a receptacle for receiving a first end of a light guide cable, a light engine with at least one LED configured to provide light transmitted from the first end of the light guide cable to a second end of the light guide cable connected to an endoscope, a connection monitor configured to determine when the second end of the light guide cable is connected to the endoscope or disconnected from the endoscope, and a light output controller configured to adjust an intensity level of the light engine according to a set intensity level when an imaging mode is selected, a first auxiliary mode when a standby mode is selected, and a second auxiliary mode when the second end of the light guide cable is disconnected.

In other features the first auxiliary mode includes a time-based function routine having a repetition of a series of duty cycle pulses, each pulse having a first maximum duty cycle and a first minimum duty cycle and including pulse widths varying in accordance with a non-linear duty cycle function, the non-linear duty cycle function including a positively biased sinusoidal function. The second auxiliary mode includes a blinking routine having a repeating duty cycle ranging from a second minimum duty cycle to a second maximum duty cycle, the first minimum duty cycle active for a blink off time and the first maximum duty cycle active for a blink on time.

In yet other features, the light source includes a light source input configured to accept user input to select the standby mode and adjust the set intensity level.

DETAILED DESCRIPTION

Figure 1:
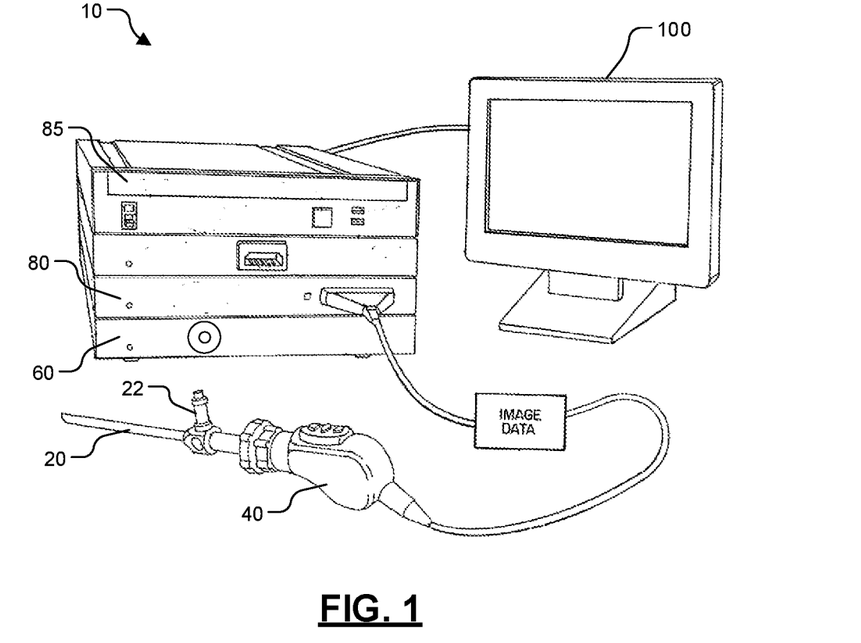
FIG. 1 is a perspective view of an exemplary endoscopic imaging system according to the principles of the present disclosure.

Referring to FIG. 1, an endoscopic imaging system 10 includes an optical endoscope 20, an imaging device 40, a light source 60, a camera control unit (CCU) 80, a display unit 85, and a display 100. The system 10 may include the endoscope 20 and the imaging device 40 (such as a detachable camera head) or alternately, the endoscope 20 and imaging device 40 may be an integral unit such as a video endoscope with an image sensor at the distal end. For ease of discussion, the system 10 as described below includes the endoscope 20 and detachable camera head 40. Although the components are described as separate, modular units, one skilled in the art would recognize they may be combined into fewer units that may perform similar functions. For example, the light source 60, CCU 80, and display unit 85 may be housed together as a single unit for receiving image data from the imaging device 40, processing the image data, and outputting it to the display 100.

Figure 2:
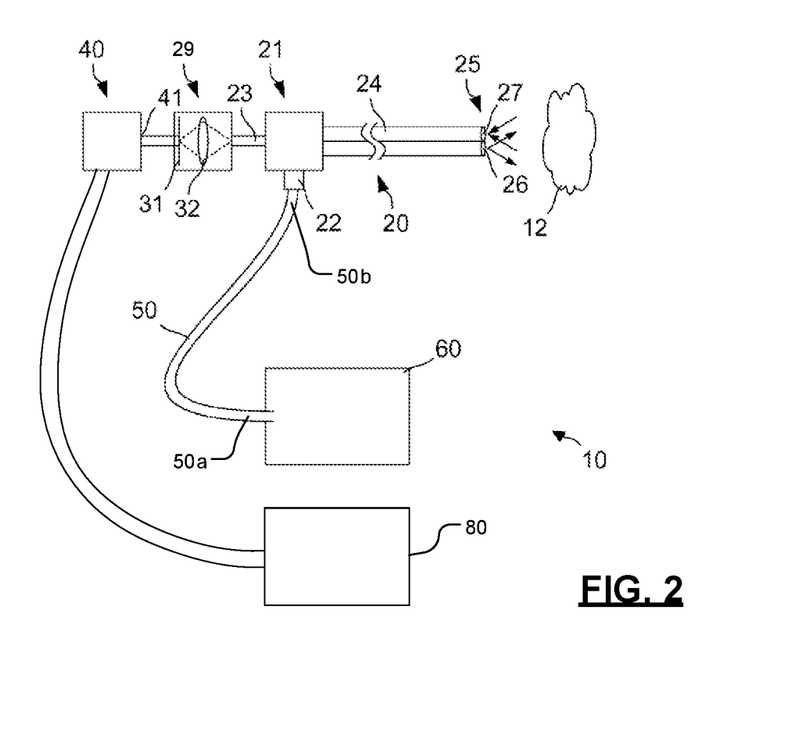
FIG. 2 is a block diagram of the endoscopic imaging system of FIG. 1 according to the principles of the present disclosure.

Referring now also to FIG. 2, a schematic diagram illustrates additional features of the system 10. The endoscope 20 includes a junction 21 with a light post 22 for receiving light generated by the light source 60 via a connected light guide cable 50. The light guide cable 50 includes a bundle of fiber optic filaments through which the light travels. The light guide cable 50 includes a first end 50a coupled to the light source 60 and a second end 50b coupled to the light post 22. The light source 60 may include any of a number of adjustable light sources with a light assembly such as a Xenon bulb, a halogen bulb, or preferably, one or more light emitting diodes (LEDs). The light may be directed from the second end 50b of the light guide cable 50 via the junction 21 to one or more light guide relays and fiber optic filaments within the endoscope 20. The light exits the endoscope 20 from a distal end 25 of the endoscope 20. The light may be dispersed by a distal light lens 26 to illuminate or irradiate the surgical site 12 with any of a variety of light including full visible spectrum light (white light), a narrow band of visible light, invisible light (infrared or ultraviolet), or any blending of light. In some instances, the light may produce a visible color as a component of the light.

The endoscope 20 includes additional components for the user to view the surgical site 12. For example, the distal end 25 may include an objective lens 27 for capturing returned light due to reflection or in other cases, emission from a fluorescing substance of tissue at the surgical site 12. The returned light forms an optical image that may be passed along the endoscope 20 via a lens relay 24 such as a Hopkins rod lens assembly. The lens relay 24 may then pass the optical image through the junction 21 to an image output lens 23 and ultimately to an eyepiece 29. The eyepiece 29 may include an additional lens system 32 to focus the optical image for use by the attached imaging device 40. An image sensor 31 captures the optical image output by the lens system 32 and transmits a raw digital image via electrical connections 41 within the image device 40. The imaging device 40 processes the raw digital image for eventual post-processing by the connected CCU 80. The CCU 80 may then pass the processed images in the form of a video signal to one of the additional components such as display unit 84 as shown in FIG. 1.

In other examples, the system 10 may include a video endoscope in place of the endoscope 20 and separate imaging device 40. In this example (not shown), the imaging device 40 may be positioned closer to the objective lens 27 to receive the optical image more directly. For example, the image sensor 31 may be small enough to be placed near the distal end 25 of the endoscope 20. The objective lens 27 may include additional features to focus the optical image directly onto the image sensor 31 making the additional components such as the lens relay 24, image output lens 23, and eyepiece 29 unnecessary. In place of the additional components, the video endoscope may include electrical connections to additional components in the handle of the video endoscope which may generate image data for processing by the CCU 80. The principles of the present disclosure are equally applicable to this example of a video endoscope.

Figure 3:
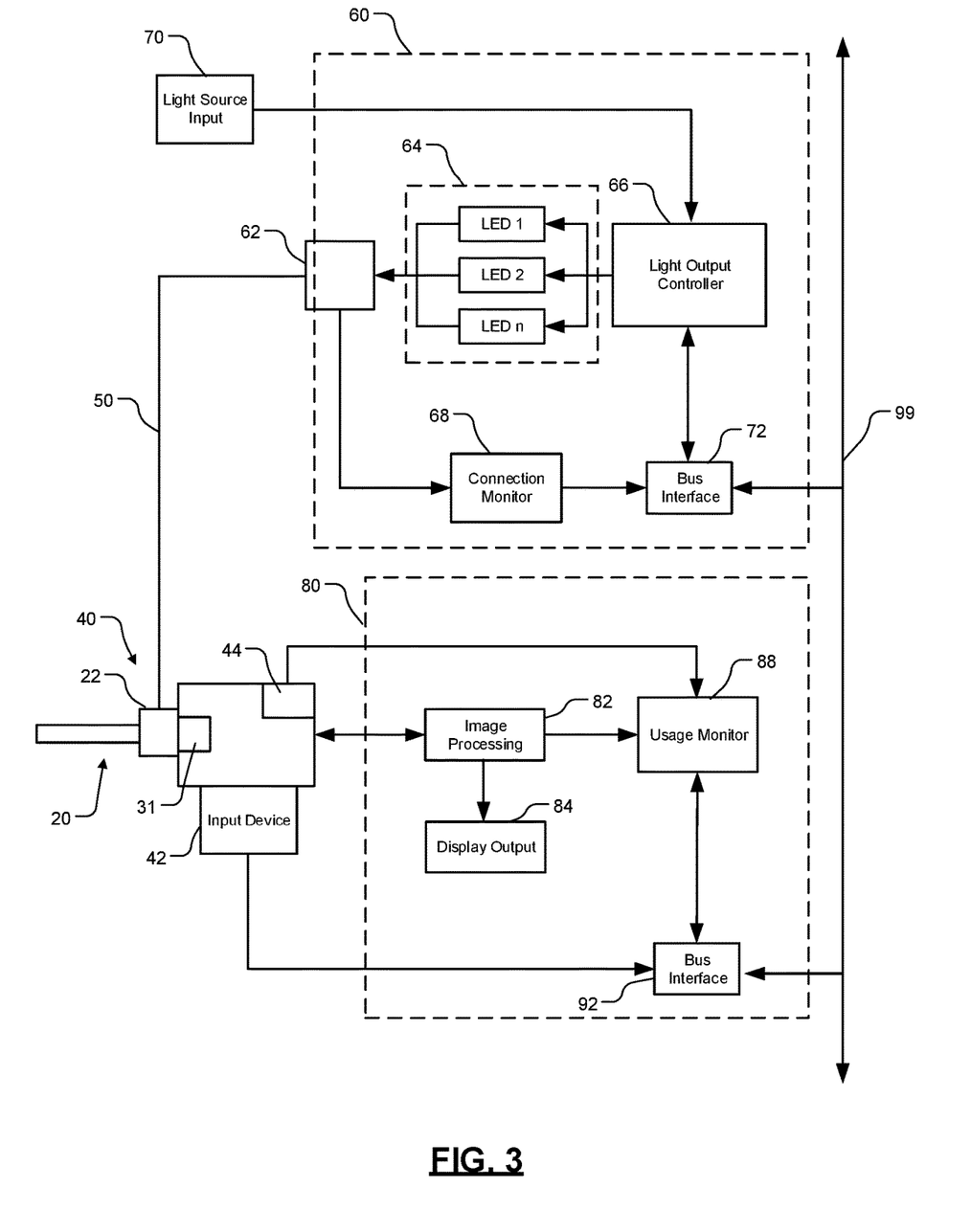
FIG. 3 is a schematic view of the endoscopic imaging system of FIG. 2 according to the principles of the present disclosure.

Referring now to FIG. 3, a schematic diagram of the system 10 illustrates additional features of the imaging device 40, light source 60, and CCU 80. The light source 60 may operate in an imaging mode or an auxiliary light mode. When in the imaging mode, the system 10 may adjust an intensity level of the light source 60 based on input from the user or input from the CCU 80. The user may adjust the intensity level using a light source input 70 or an input device 42 of the imaging device 40. The CCU 80 may also adjust the intensity level to improve the quality of the image data provided by the image sensor 31. When in the standby mode, the intensity level set by the user or CCU 80 may be overridden and adjusted according to an auxiliary mode. The user may select the standby mode or the CCU 80 may select the standby mode as described below. In other situations, the intensity level set by the user or CCU 80 may be overridden and adjusted according to other auxiliary modes as described further below.

As shown in the exemplary figure, the imaging device 40 includes the camera head coupled with the endoscope 20. The camera head includes the image sensor 31 and the input device 42. The camera head may further include a movement sensor 44. The image sensor 31 receives optical images from the endoscope 20 and generates image data for image processing by the CCU 80. The input device 42 may be one or more buttons, control pads, or joysticks for inputting commands to the imaging device 40 such as entering commands for controlling one or more features of the system 10 including the light source 60. The movement sensor 44 may include an inertia measurement unit (IMU), gyroscope, accelerometer(s), or the like as known in the art for determining movement and orientation of the imaging device 40 and/or the connected endoscope 20. Data provided by the image sensor 31, input device 42, and movement sensor 44 may be used by the CCU 80 to execute various methods for imaging the surgical site 12 and controlling the light source 60 in the imaging mode.

The light source 60 includes a light guide receptacle 62, a light engine or lamp 64, and a light output controller 66. The light guide receptacle 62 releasably couples with the first end 50a of the light guide cable 50. The light engine 64 may include one light or a plurality of lights. In the present example, the light engine 64 includes light-emitting diodes (LEDs). The light engine 64 may include any number (n) of LEDs and is shown in the figure as including a first LED 1, a second LED 2, and up to a last LED n. In some examples, the LEDs may be color LEDs which include the primary colors of red (R), green (G), and blue (B) light such that first LED 1 produces red light, second LED 2 produces green light, and last LED n produces blue light. The LEDs may be blended by the light output controller 66 to produce various colors of illumination. For example, first LED 1 may provide a range of wavelengths within the full-visible spectrum of light commonly referred to as white light. Second LED 2 may provide a narrower spectrum of light such as, for example, light for various applications known in the art including, but not limited to fluorescent imaging such as for photodynamic diagnosis (PDD), multispectral imaging, hyperspectral imaging, indocyanine green (ICG) imaging, and the like.

The light output controller 66 may adjust one or more output levels of the LEDs of the light engine 64 by varying power supplied to each of the LEDs. This may be accomplished by varying a duty cycle or pulse width modulation of the power applied to each of the LEDs. The light is delivered to the light guide cable 50 through the light guide receptacle 62. The light guide receptacle 62 may further include a light collimator to focus the light from the LEDs into the optical fibers. The light source 60 may also include a connection monitor 68, the light source input 70, and a light bus interface 72. The light source input 70 may include one or more buttons to adjust the intensity level of the LEDs from 0% to 100% intensity. The light source input 70 may include a standby button to command the light source 60 to enter into the standby mode and cause the light output controller 66 to output a standby message to the light bus interface 72.

As noted above, the connection monitor 68 may determine when the light guide cable 50 is disconnected and connected with the light source 60. For example, the light guide cable 50 and light source 60 may include mechanical features, optical features, electrical circuitry, and software for detecting whether the second end 50*b* of the light guide cable 50 is connected to the light post 22 of the endoscope 20. In the present example, the connection monitor 68 may determine whether the light guide cable 50 is connected to the endoscope 20 and output a connected state message to the light bus interface 72 or is disconnected from the endoscope 20 and output a disconnected state message to the light bus interface 72 as described further below.

The camera control unit 80 includes an image processing module 82, a display output module 84, a usage monitor 88, and a CCU bus interface 92. The image processing module 82 may receive image data from the imaging device 40 which may be processed for display on the monitor 100 by the display output module 84 or recorded or processed by another component. In some examples, the display output module 84 may be included with the display unit 85. The user may use the input device 42 to adjust the intensity level of the light engine 64. Input device 42 may communicate via the CCU bus interface 92 to the light source 60 over the communication link 99. The intensity level may be transmitted via the light bus interface 72 to the light output controller 66.

The usage monitor 88 may detect when the system 10 is no longer being used in the imaging mode, select the standby mode for the light source 60, and override the set light level using an auxiliary mode. For example, the image processing module 82 may provide processed image data and movement sensor 44 may provide movement data to the usage monitor 88. If the image data indicates little or no change in the imaging of the surgical site 12 or other captured scene and the movement data indicates little or no movement, then the usage monitor 88 may select the standby mode and send the standby message over the CCU bus interface 92 and communication link 99 to the light source 60. The light source 60 may then adjust the intensity level according to an auxiliary mode.

Likewise, the usage monitor 88 may detect when the system 10 has experienced a disconnected light guide cable and override the set light level using another auxiliary mode. For example, the image processing module 82 may provide processed image data and movement sensor 44 may provide movement data to the usage monitor 88. If the image data indicates a significant change in the brightness of the imaging of the surgical site 12 and the movement data indicates continued movement, then the usage monitor 88 may determine the light guide cable 50 is disconnected and send the disconnected message over the CCU bus interface 92 and communication link 99 to the light source 60.

The image processing module 82 and movement sensor 44 may be used to identify other combinations of imagery and movements that correspond to a disconnected light guide cable. For example, a fade in detected image brightness, due to a low level of detected light by the image sensor 31, for a period of time greater than a time threshold while the intensity level of the light engine 64 is greater than an intensity threshold may indicate the light guide cable is disconnected. If movement data (acceleration, etc.) from the movement sensor 44 indicates the endoscope 20 and imaging device 40 are still being moved while the light source 60 outputs an intensity level greater than the intensity threshold, but the detected image brightness has decreased, the usage monitor 88 may determine the light guide cable 50 is disconnected and output a disconnected message to the CCU bus interface 92 over the communication link 99 to the light source 60. The light source 60 may then adjust the intensity level according to another auxiliary mode.

Figure 4:
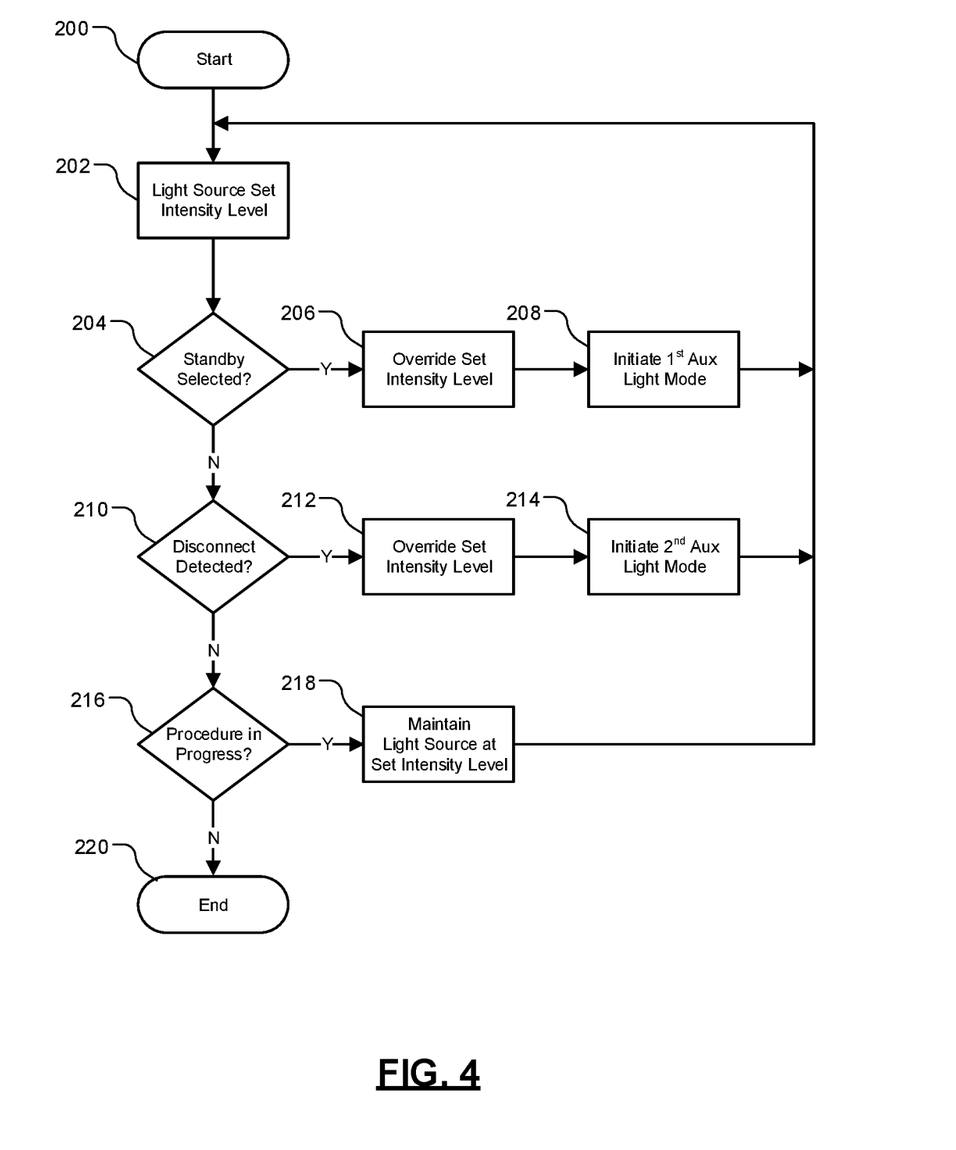
FIG. 4 is a flowchart illustrating exemplary control executed by software and hardware of the endoscopic imaging system according to the principles of the present disclosure.

Referring now to FIG. 4, a flowchart illustrates exemplary steps of a method according to the principles of the present disclosure. At step 200, the system 10 may begin normal operation in the imaging mode in which the endoscope 20, imaging device 40, light source 60, and CCU 80 are connected and configured to provide imaging of the surgical site 12. At step 202, the light source 60 has been powered on and the user or CCU 80 has adjusted the intensity level to a set intensity level. This may be due to actuation by the user of light source input 70 to a value greater than 0% or by another user input such as an on/off switch. As the user performs a procedure at the surgical site 12, the light source 60 may further adjust the light output level based on the user input or control by the CCU 80 in the imaging mode.

At step 204, software executing on the system 10 determines if standby mode has been selected by the user or the usage monitor 88. For example, the user may select standby mode by choosing the mode using the light source input 70, the input device 42, or another menu of the light source 60, CCU 80 or other user interface of the system 10. The user selection of standby mode may be communicated via the standby message over the communication link 99. Alternately, the usage monitor 88 may evaluate whether the standby mode should be activated based on determinations by the image processing module 82 and movement sensor 44 as described above. In either instance, a bit or other variable provided by the standby message may indicate to the light output controller 66 that standby mode is selected. At step 206, the light output controller 66 may then override the intensity level previously set at step 202 and select a first auxiliary light mode corresponding to the standby mode. At step 208, the light output controller 66 adjusts the intensity level according to the first auxiliary light mode to indicate to the user via the second end 50*b* of the light guide cable 50 that the light source 60 is in standby mode. Light may exit the distal end of the endoscope 20 if the light guide cable 50 remains connected.

If standby mode is not selected at step 204, the system 10 evaluates the status of the light guide cable 50 and light source 60 at step 210. For example, the connection monitor 68 may evaluate whether the light guide cable 50 remains connected to the light post 22 by checking the light guide receptacle 62 for a completed circuit as noted above. Alternately, the usage monitor 88 may evaluate whether the light guide cable 50 remains connected to the light post 22 based on data provided by the image processing module 82 and movement sensor 44. If the light guide cable 50 become disconnected from the light post 22, the connection monitor 68 or usage monitor 88 outputs the disconnected message via a bit or other variable in the software which indicates to the light output controller 66 that the light guide cable 50 is disconnected. At step 212, the light output controller 66 may then override the intensity level set by the user previously at step 202 and select a second auxiliary light mode to indicate to the user via the second end 50*b* of the light guide cable 50 that the light guide cable 50 is disconnected from the light post 22.

If standby mode is not selected and no disconnected light guide cable is detected, the method proceeds to step 216 where the procedure may continue in imaging mode. The light source 60 may be maintained at the intensity level set by the user or the CCU 80 in step 218. The method ends at step 220 when the imaging mode is no longer active and the system 10 is powered off.

Referring now to FIGS. 5A-5F, six exemplary auxiliary modes are depicted using several graphs showing % duty cycle of the light engine 64 vs. time. Various combinations of the auxiliary modes may be used to indicate to the user the status of the light source 60 and light guide cable 50.

Figure 5A:
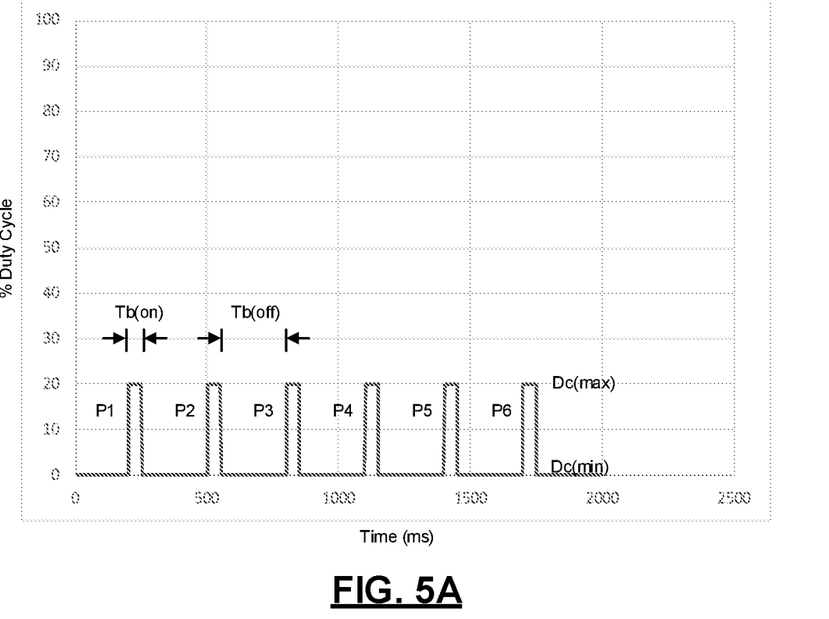
FIGS. 5A-5F are auxiliary modes for adjusting an intensity level of light provided by the light source according to the principles of the present disclosure.

As shown in FIG. 5A, one exemplary auxiliary mode may include a blinking routine. Here, six pulses labeled P1-P6 are provided in a 2000 millisecond timeframe. Each pulse P1-P6 may be the same color of light. The light engine 64 may drive a single LED or a plurality of LEDs to produce full spectrum visible light (white light) or a color of light such as red, green, or blue light. If a plurality of LEDs is provided including red, green, and blue LEDs, the single color of light may be any blended color. The light output controller 66 may drive the LED(s) from a minimum duty cycle Dc(min) such as 0% duty cycle to a maximum duty cycle Dc(max) such as a 20% duty cycle (and up to 100% duty cycle) and hold for a predetermined blink on time Tb(on) such as 50 milliseconds. The light output controller 66 may then decrease from the Dc(max) to the Dc(min) and hold for a predetermined blink off time Tb(off) such as 250 milliseconds.

Figure 5B:
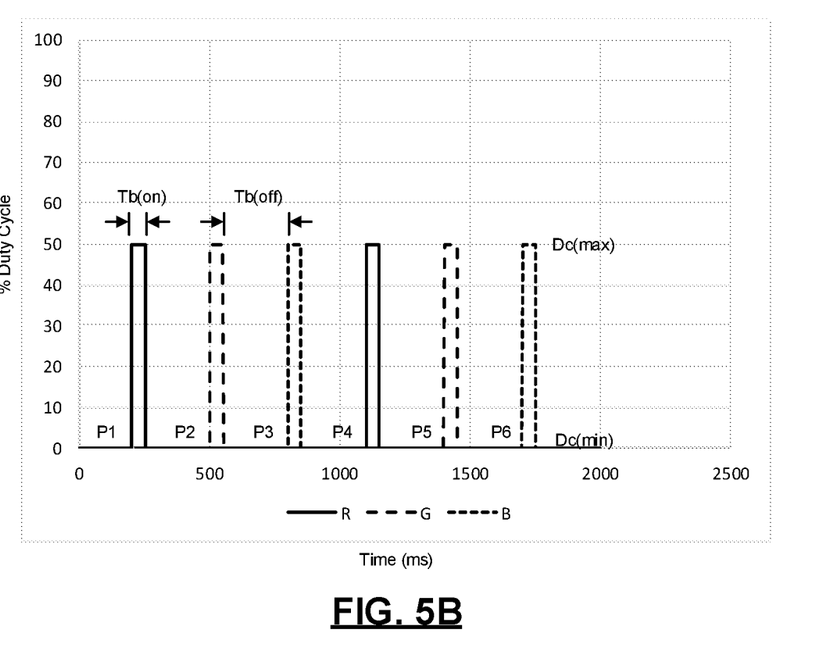
Figure 5C:
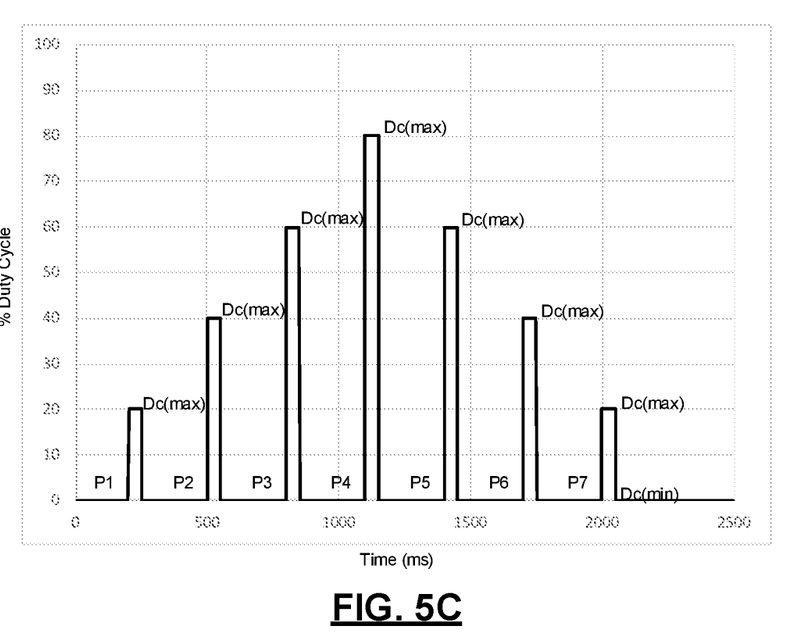

Alternately, as shown in FIG. 5B, each pulse P may be a different color of light provided by a different combination of color LEDs. For example, P1 may be red, P2 may be green, and P3 may be blue. The colors may repeat in a sequence and P4 may be red, P5 may be green, and P6 may be blue. Dc(max) may be 50% duty cycle. Likewise, each pulse P may include a different minimum duty cycle Dc(min) and/or a different maximum duty cycle Dc(max) as shown in FIG. 5C. Though Tb(on) and Tb(off) are shown as the same values for all examples in FIGS. 5A-5C, the blink on time Tb(on) and blink off time Tb(off) may vary between pulses as well. Thus, any combination of pulses P may be provided and may be customized to produce different pulse colors, durations, and intensity levels. Each combination of pulses may be used to indicate to the user a different status of the system 10, such as for example, a disconnected light guide cable.

Figure 5D:
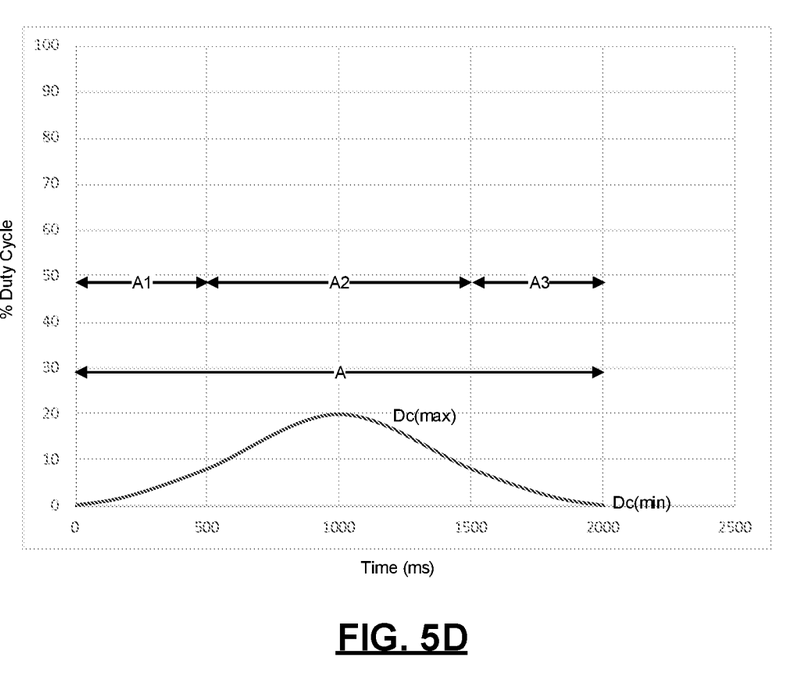

As shown in FIG. 5D, another exemplary auxiliary mode may include a time-based function routine which may provide a continuous or near-continuous output of light according to a predetermined function. For example, the light engine 64 may vary the duty cycle Dc according to a time-based function to produce an effect similar to a cadence of typical human breathing. The time-based function routine may include a linear duty cycle function having a positive slope increasing from Dc(min) to Dc(max) followed by a negative slope decreasing from Dc(max) to Dc(min). The time-based function routine may include a non-linear duty cycle function including a positively biased sinusoidal function having a period A during which the duty cycle increases to the maximum duty cycle Dc(max) and decreases to the minimum duty cycle Dc(min). Similar to the blinking routine, the light engine 64 may drive a single LED or a plurality of LEDs to produce full spectrum visible light (white light) or a single color of light such as red, green, or blue light. If a plurality of LEDs is provided including red, green, and blue LEDs, the single color of light may be any blended color.

Alternately, the time-based function routine may produce a different color of light at different times during period A. For example, during a first portion A1 of period A, the color of the LED may be a first color; during a second portion A2 of period A, the color of the LED may be a second color; and during a third portion A3 of period A, the color of the LED may be a third color. The LED may transition from the first color to the second color to the third color continuously through a color spectrum. Thus, multiple colors may be used in the first period. If red, green, and blue LEDs are present, the various combinations of LEDs may be driven to produce different colors at different times each period A. For example, a red LED may be driven according to the duty cycle Dc from times T=0 to T=500, a green LED may be driven according to the duty cycle Dc from times T=500 to T=1000, and the blue LED may be driven according to the duty cycle from times T=1000-2000. The red, green, and blue LEDs may be independently controlled to produce a continuously changing color scheme throughout the first period, cycling from the first color at time T=0 to the second color at time T=1000 and back to the first color at T=2000.

Figure 5E:
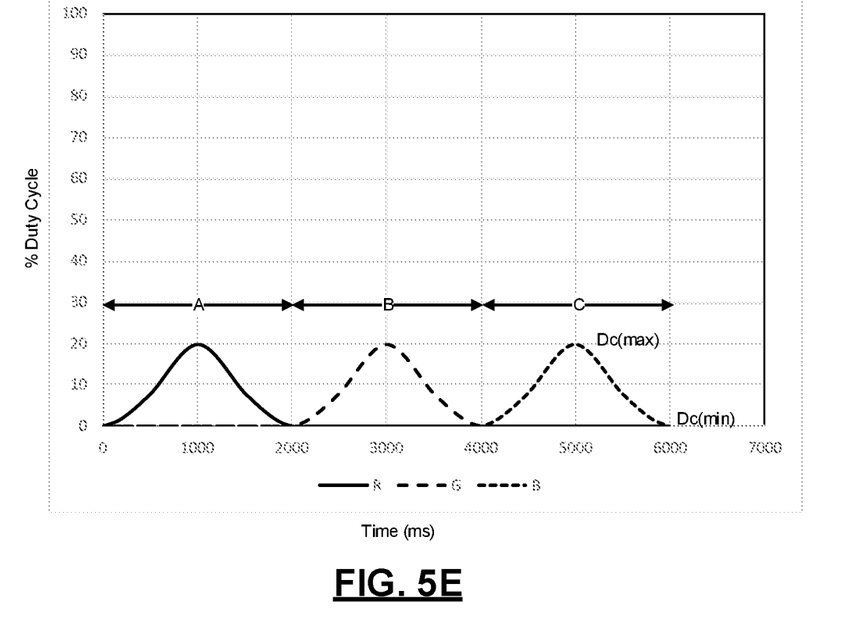
Figure 5F:
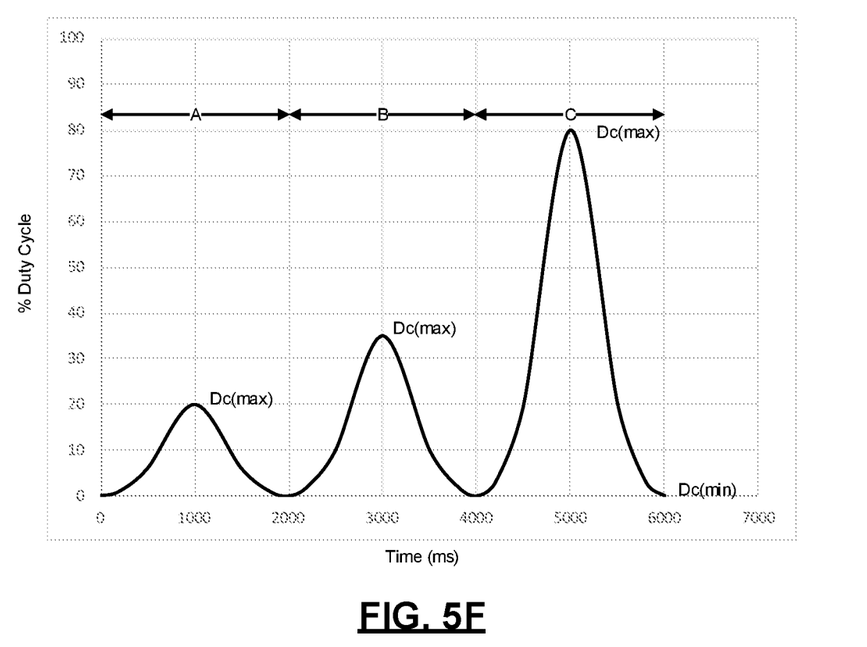

In FIG. 5E, three sequential periods A, B, and C illustrate another example of the time-based function. In a first period A, the color of the LED may be red. In a second period B, the color of the LED may be green. In a third period C, the color of the LED may be blue. Likewise, each period A, B, and C may include a different minimum duty cycle Dc(min) and/or a different maximum duty cycle Dc(max) as shown in FIG. 5F. Thus, any combination of periods may be provided and may be customized to produce different colors, durations, and intensities of light according to a time-based function. Each combination may be used to indicate to the user a different status of the imaging system 10, such as for example, that the system 10 is in standby mode.

Specific values for the duty cycle and time and specific colors are provide for exemplary purposes only. Dc(max), Dc(min), Tb(on) and Tb(off) and selected colors may be any combination of values which would be perceptible to alert the user that the auxiliary mode is adjusting the light source 60 and imaging mode is no longer active.

Referring back to FIG. 4, when the standby mode has been selected at step 204, the light output controller 66 may adjust the intensity level according to one of the auxiliary modes such as, for example, the auxiliary mode shown in FIG. 5D. Thus, when in standby mode, the light output controller 66 drives the LEDs to output light according to the time-based function routine and the second end 50*b* of the light guide cable 50 will output light that appears to mimic "breathing." This is an improvement over the prior art which simply reduces the intensity level of the light to nothing or a "safe" low level. From afar, the "breathing" cadence of the light emitted from the light guide cable 50 or endoscope 20 readily identifies to the user that the light source 60 is still on but is in standby mode.

When the light guide cable 50 disconnection is detected at step 210, the light output controller 66 may adjust the intensity level according to another one of the auxiliary modes such as, for example, the mode shown in FIG. 5A. Thus, when the disconnect occurs, the light output controller 66 drives the LEDs to output light according to the blinking routine. Thus, the second end 50*b* of the light guide cable 50 will output light at a reduced duty cycle of 20% and blink repeatedly. This is an improvement over the prior art which simply reduces the intensity level of the light to nothing or a "safe" low level. From afar, the blinking of the light emitted from the disconnected second end 50*b* readily identifies to the user that the light source 60 is still on and the light guide cable 50 is disconnected.

The principles of the present disclosure may be applied to other endoscopic imaging systems 10 and the light guide cable 50 may be used to visually communicate to the user additional statuses related to the functioning of the imaging device 40, the light source 60, the CCU 80, or another component connected, for example, over the communication link 99. This visual indication provided by the light source 60, whether the light guide cable 50 or from the endoscope 20, may be more readily discernable by the user when the light source 60, CCU 80, or display 100 are located far away or obstructed from the user's view. For example, the light output control module 66 may receive messages over the communication link 99 from any of a number of other connected components. The messages may indicate one or more statuses of the other connected components. In response to receiving the messages, the light output controller 66 may activate additional auxiliary light modes disclosed in FIGS. 5A-5F or various other combinations not disclosed herein but ascertainable by a person of ordinary skill.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. An endoscope system
comprising: a light source including:
a receptacle for receiving a first end of a light guide cable;
a light engine including at least one LED configured to provide a light output transmitted from the first end of the light guide cable to a second end of the light guide cable connected to an endoscope;
an input for setting a set intensity level; and
a light output controller configured to adjust the light output of the light engine according to the set intensity level; and
a camera control unit having a usage monitor configured to process an image data and a movement of the endoscope provided by a movement sensor configured to detect a physical movement of the endoscope to determine if the light guide cable is disconnected; and wherein
the light source is automatically placed in a standby mode when no movement of the endoscope is detected, and, in the standby mode, the light output controller overrides the set intensity level, and the output of the light engine is operated in a first auxiliary mode;
when the light guide cable is disconnected, the light output controller overrides the set intensity level and the output of the light engine is operated in a second auxiliary mode; and
the output of the light engine remains at the set intensity level when the light cable is connected and the light source is not in the standby mode, wherein the first auxiliary mode is different than the set intensity level, and the second auxiliary mode is different than the first auxiliary mode so as to visibly distinguish between when the light source is in the standby mode and when the light guide has been disconnected.

2. The endoscope system of claim 1, wherein the light output controller in the first auxiliary mode adjusts an intensity level of the light output according to a time-based function routine.

3. The endoscope system of claim 2, wherein the time-based function routine includes a repeating duty cycle, Dc, in which the light output controller adjusts the intensity level from a Dc(min) to a Dc(max) followed by a negative slope decreasing from the Dc(max) to the Dc(min).

4. The endoscope system of claim 2, wherein the time-based function routine includes a repetition of a series of duty cycle pulses, each pulse having a maximum duty cycle and a minimum duty cycle and including pulse widths varying in accordance with a non-linear duty cycle function, the non-linear duty cycle function including a positively biased sinusoidal function.

5. The endoscope system of claim 1, further comprising a light source input configured to accept user input to select the standby mode and adjust the set intensity level.

6. The endoscope system of claim 1, further comprising a connection monitor configured to determine when the second end of the light guide cable is connected to the endoscope or disconnected from the endoscope.

7. The endoscope system of claim 6, wherein when the connection monitor detects a disconnected light guide cable, the light output controller selects the second auxiliary mode and the light output controller in the second auxiliary mode adjusts the intensity level of the light output according to a blinking routine.

8. The endoscope system of claim 7, wherein the blinking routine includes a repeating duty cycle ranging from a minimum duty cycle to a maximum duty cycle, the minimum duty cycle active for a blink off time and the maximum duty cycle active for a blink on time.

9. An endoscope system comprising:
a light guide cable including a first end opposite a second end;
an imaging device including a movement sensor configured to detect a physical movement of the imaging device, the imaging device coupled to the second end of the light guide cable;
a light source having a receptacle, a light output controller and a light engine, the receptacle configured to releasably couple with the first end of the light guide, the light engine including at least one LED configured to provide a light output transmitted from the first end of the light guide cable to a second end of the light guide cable connected to the imaging device, the light output controller configured to adjust an intensity level of the light engine;
an input for setting a set intensity level;
a camera control unit having a usage monitor configured to process at least one of an image processing and a movement of the imaging device to determine if the light guide cable is disconnected, wherein the light guide cable is determined to be disconnected when an image data indicates a change in brightness and the imaging device is simultaneously moving; and wherein the light output controller adjusts the intensity level of the light engine according to the set intensity level when an imaging mode is selected, wherein the light output controller is configured to override the set intensity level and operate in a second auxiliary mode when the second end of the light guide cable is disconnected so as to visibly distinguish between when the light source is in a standby mode and when the light guide has been disconnected, wherein, in the standby mode, the light output controller overrides the set intensity level, and the output of the light engine is operated in a first auxiliary mode, and wherein the second auxiliary mode is different from the first auxiliary mode.

10. The endoscope system of claim 9, wherein the first auxiliary mode adjusts an intensity level of the light output according to a blinking routine.

11. The endoscope system of claim 10, wherein the blinking routine includes a repeating duty cycle ranging from a minimum duty cycle to a maximum duty cycle, the minimum duty cycle active for a blink off time and the maximum duty cycle active for a blink on time.

12. The endoscope system of claim 9, wherein the light output controller is further configured to adjust the intensity level according to a second auxiliary mode when a standby mode is selected.

13. The endoscope system of claim 12, wherein the light output controller in the second auxiliary mode adjusts the intensity level of the light output according to a time-based function routine.

14. The endoscope system of claim 13, wherein the time-based function routine includes a repeating duty cycle, Dc, in which the light output controller adjusts the intensity level to increase and decrease from a Dc(min) to a Dc(max) followed by a negative slope decreasing from the Dc(max) to the Dc(min).

15. The endoscope system of claim 13, wherein the time-based function routine includes a repetition of a series of duty cycle pulses, each pulse having a maximum duty cycle and a minimum duty cycle and including pulse widths varying in accordance with a non-linear duty cycle function, the non-linear duty cycle function including a positively biased sinusoidal function.

16. The endoscope system of claim 12, further comprising a light source input configured to accept user input to select the standby mode and adjust the set intensity level.

* * * * *